(12) United States Patent
Kumagai et al.

(10) Patent No.: US 6,710,181 B2
(45) Date of Patent: Mar. 23, 2004

(54) IMIDAZOLE/ORGANIC MONOCARBOXYLIC ACID SALT DERIVATIVE REACTION PRODUCT, METHOD FOR PRODUCING THE SAME, AND SURFACE TREATMENT AGENT, RESIN ADDITIVE AND RESIN COMPOSITION USING THE SAME

(75) Inventors: Masashi Kumagai, Kitaibaraki (JP); Katsuyuki Tsuchida, Kitaibaraki (JP)

(73) Assignee: Nikko Materials Co., Ltd., Tokyo (JP)

( * ) Notice: Subject to any disclaimer, the term of this patent is extended or adjusted under 35 U.S.C. 154(b) by 82 days.

(21) Appl. No.: 09/936,073

(22) PCT Filed: Feb. 6, 2001

(86) PCT No.: PCT/JP01/00819

§ 371 (c)(1), (2), (4) Date: Sep. 5, 2001

(87) PCT Pub. No.: WO01/77119

PCT Pub. Date: Oct. 18, 2001

(65) Prior Publication Data

US 2003/0088108 A1 May 8, 2003

(30) Foreign Application Priority Data

Apr. 7, 2000 (JP) .......................... 2000-106274
Jul. 27, 2000 (JP) .......................... 2000-226757

(51) Int. Cl.$^7$ .................................................. C07F 7/02
(52) U.S. Cl. ................................... 548/110; 548/341.6
(58) Field of Search ............................. 548/110, 341.6

(56) References Cited

U.S. PATENT DOCUMENTS 5,258,522 A 11/1993 Tsuchida et al.

FOREIGN PATENT DOCUMENTS

| EP | 0 526 847 A1 | 2/1993 |
|---|---|---|
| JP | 51-35711 | 10/1976 |
| JP | 54-6701 | 3/1979 |
| JP | 58-7077 | 2/1983 |
| JP | 5-186479 | 7/1993 |
| JP | 9-114096 | 5/1997 |
| JP | 10-120690 | 5/1998 |

OTHER PUBLICATIONS

Improved Adhesion Between Kapton Film and Copper Metal by Silane–Coupling Reactions, by N. Inagaki et al, Journal of Applied Polymer Science, vol. 73, No. 9, Aug. 29, 1999, pp. 1645–1654.

Primary Examiner—Joseph K. McKane
Assistant Examiner—Kamal Saeed
(74) Attorney, Agent, or Firm—Flynn, Thiel, Boutell & Tanis, P.C.

(57) ABSTRACT

The present invention provides a novel imidazole/organic monocarboxylic acid salt derivative reaction product capable of improving the adhesion between a resin and a metal such as copper, steel or aluminum, or an inorganic material such as glass fiber, silica, aluminum oxide or aluminum hydroxide, a method for producing this imidazole/organic monocarboxylic acid salt derivative reaction product, and a surface treatment agent, resin additive and resin composition that use this imidazole/organic monocarboxylic acid salt derivative reaction product.

The above imidazole/organic monocarboxylic acid salt derivative reaction product is obtained by reacting an imidazole compound represented by undermentioned general formula (1) with a silane compound having a glycidoxy group represented by undermentioned general formula (2) at 80 to 200° C., and then reacting the product thus obtained with an organic monocarboxylic acid at 50 to 200° C.

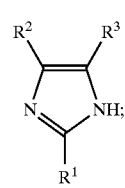

(1)

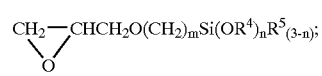

(2)

3 Claims, 4 Drawing Sheets

IMIDAZOLE/ORGANIC MONOCARBOXYLIC ACID SALT DERIVATIVE REACTION PRODUCT, METHOD FOR PRODUCING THE SAME, AND SURFACE TREATMENT AGENT, RESIN ADDITIVE AND RESIN COMPOSITION USING THE SAME

TECHNICAL FIELD

The present invention relates to a novel imidazole/monocarboxylic acid derivative, and also to a surface treatment agent that has this imidazole/monocarboxylic acid derivative as an active ingredient and is for improving the adhesion between a metal such as copper, steel or aluminum or an inorganic material such as glass fiber, silica, aluminum oxide or aluminum hydroxide and a resin, a resin additive that has this imidazole/monocarboxylic acid derivative as an active ingredient and is for improving the adhesive strength and mechanical strength of a resin such as an epoxy resin, and a resin composition—in particular a polyimide resin composition—that contains this imidazole/monocarboxylic acid derivative.

BACKGROUND ART

A board of an electronic device is made by heating copper foil and a phenol-resin-impregnated paper substrate, an epoxy-resin-impregnated glass substrate or the like while pressurizing to produce a copper-clad laminate, and then forming an electric network by etching, and mounting elements such as semiconductor devices on top.

During the manufacturing process, the copper foil is bonded to the substrate, and they are heated, immersed in acidic or alkaline solutions, a resist ink applied thereto, soldered, and hence the copper foil and the substrate are required to have various properties. To satisfy these requirements, with regard to the copper foil, studies have been carried out subjecting the copper foil to brass layer formation treatment (Japanese Patent Publication Nos. S51-35711 and S54-6701), chromate treatment, zinc-chromium mixture coating treatment in which the coating includes zinc or zinc oxide and chromium oxide (Japanese Patent Publication No. S58-7077), treatment with a silane coupling agent, and the like. Moreover, with regard to the resin, the requirements are satisfied by changing the type of resin and/or curing agent and/or the mixing proportions thereof, by adding additives, and so on. Moreover, in the case of glass fiber, surface treatments using a silane coupling agent or the like have been studied. However, in recent years, there have been advances in miniaturization of printed circuits, and the properties required of the boards used in electronic devices have become ever more stringent.

To cope with the required improvement in etching precision that goes along with the above, the Matte side of the copper foil bonded to the prepreg is required to have a lower surface roughness (i.e. a low profile). However, the surface roughness of the Matte side produces an anchoring effect so as to bond the prepreg tightly, and hence the requirement of a low profile goes against improving the adhesive strength, meaning that the reduction in the anchor effect upon lowering the profile must be compensated for by improving the adhesive strength by another means.

Moreover, a composite material in which an inorganic material such as silica or alumina is filled into an epoxy resin matrix is used as an electrically insulating casting material used, for example, in high voltage/high capacity devices and in sealing semiconductors in power plants. Various electrical and mechanical properties are required of such a material, and to satisfy these requirements it is necessary to improve the adhesion between the inorganic material and the resin. Measures such as adding a silane coupling agent into the resin or subjecting the inorganic material to surface treatment with a silane coupling agent have been proposed, but further improvement of the resin/inorganic material interface is required.

DISCLOSURE OF THE INVENTION

An object of the present invention is to provide a novel imidazole/organic monocarboxylic acid salt derivative reaction product that is capable of meeting these requirements, that is, that improves the adhesion between a metal such as copper, steel or aluminum or an inorganic material such as glass fiber, silica, aluminum oxide or aluminum hydroxide and a resin. Further, another object of the present invention is to provide a method for producing this imidazole/organic monocarboxylic acid salt derivative reaction product, and a surface treatment agent, resin additive and resin composition that use this imidazole/organic monocarboxylic acid salt derivative reaction product.

The inventors of the present invention carried out assiduous studies, and as a result discovered: if a metal or an inorganic material is subjected to surface treatment with an imidazole/organic monocarboxylic acid salt derivative reaction product obtained by reacting a specific imidazole compound with a silane compound having a glycidoxy group and then reacting with an organic monocarboxylic acid, then the adhesion of the metal or the inorganic material to a resin is improved; and furthermore, if such an imidazole/organic monocarboxylic acid salt derivative reaction product is added to a resin such as an epoxy resin, then the curing reaction of the resin is promoted and moreover the adhesive strength and the mechanical strength of the resin are improved.

The present invention was achieved based on the above findings, and is summarized as follows:

(1) An imidazole/organic monocarboxylic acid salt derivative reaction product obtained by reacting an imidazole compound represented by undermentioned general formula (1) with a silane compound having a glycidoxy group represented by undermentioned general formula (2) at 80 to 200° C., and then reacting with an organic monocarboxylic acid at 50 to 200° C.;

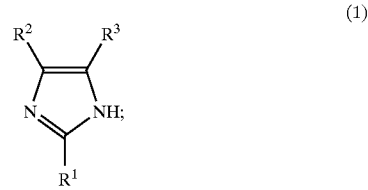

-continued

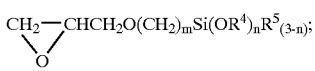
(2)

where, in general formulae (1) and (2), $R^1$, $R^2$ and $R^3$ are each independently a hydrogen atom, a vinyl group, or an alkyl group having 1 to 20 carbon atoms, while $R^2$ and $R^3$ may together form an aromatic ring; $R^4$ and $R^5$ are each independently an alkyl group having 1 to 5 carbon atoms; m is an integer between 1 and 10; and n is an integer between 1 and 3.

(2) A method for producing the imidazole/organic monocarboxylic acid salt derivative reaction product as described in (1) above, comprising: reacting an imidazole compound represented by undermentioned general formula (1) with a silane compound having a glycidoxy group represented by undermentioned general formula (2) at 80 to 200° C.; and subsequently reacting with an organic monocarboxylic acid at 50 to 200° C.;

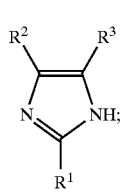
(1)

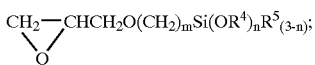
(2)

where, in general formulae (1) and (2), $R^1$, $R^2$, $R^3$, $R^4$, $R^5$, m and n are as defined in (1) above.

(3) A surface treatment agent having the imidazole/organic monocarboxylic acid salt derivative reaction product as described in (1) above as an active ingredient.

(4) A resin additive having the imidazole/organic monocarboxylic acid salt derivative reaction product as described in (1) above as an active ingredient.

(5) A resin composition containing the imidazole/organic monocarboxylic acid salt derivative reaction product as described in (1) above.

(6) A polyimide resin composition containing the imidazole/organic monocarboxylic acid salt derivative reaction product as described in (1) above.

Following is a more detailed description of the present invention.

In above-mentioned general formulae (1) and (2), if any of $R^1$, $R^2$ or $R^3$ is an alkyl group, then this alkyl group has 1 to 20 carbon atoms, preferably 1 to 12 carbon atoms. Moreover, if $R^2$ and $R^3$ together form an aromatic ring, then this aromatic ring is preferably a benzene ring.

The imidazole/organic monocarboxylic acid salt derivative reaction product of the present invention can be manufactured by reacting an imidazole compound represented by undermentioned general formula (1) with a silane compound having a glycidoxy group represented by undermentioned general formula (2) at 80 to 200° C., and then reacting with an organic monocarboxylic acid at 50 to 200° C. The reaction mechanism is complicated, with networking through siloxane bonds occurring in part, but the main reactions can be represented by the following formulae.

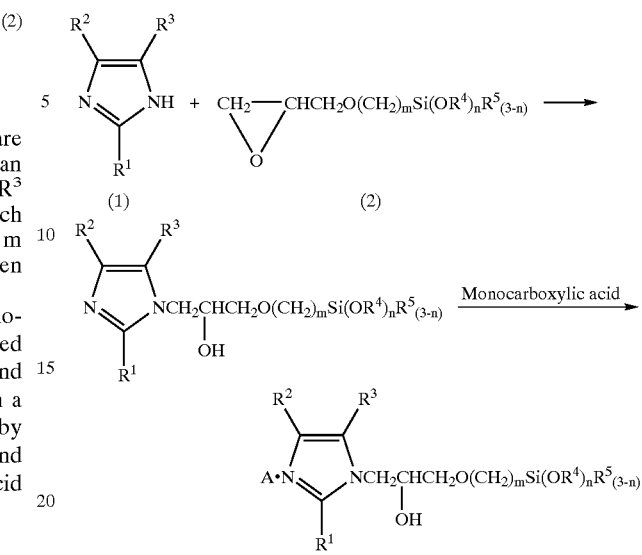

In the above general formula, A indicates the organic monocarboxylic acid.

Preferable examples of the imidazole compound represented by above-mentioned general formula (1) include imidazole, 2-alkylimidazoles, 2,4-dialkylimidazoles and 4-vinylimidazole. Of these, particularly preferable ones include imidazole; as 2-alkylimidazoles, 2-methylimidazole, 2-ethylimidazole and 2-undecylimidazole; and as a 2,4-dialkylimidazole, 2-ethyl-4-methylimidazole. Moreover, examples of the silane compound having a glycidoxy group represented by above-mentioned general formula (2) are 3-glycidoxypropyltrialkoxysilanes, 3-glycidoxypropyldialkoxyalkylsilanes and 3-glycidoxypropylalkoxydialkylsilanes. Of these, particularly preferable ones include, as 3-glycidoxypropyltrialkoxysilanes, 3-glycidoxypropyltrimethoxysilane and 3-glycidoxypropyltriethoxysilane; as a 3-glycidoxypropyldialkoxyalkylsilane, 3-glycidoxypropyldimethoxymethylsilane; and as a 3-glycidoxypropylalkoxydialkylsilane, 3-glycidoxypropylethoxydimethylsilane. Moreover, as the organic monocarboxylic acid, a saturated aliphatic monocarboxylic acid, an unsaturated aliphatic monocarboxylic acid, an aromatic monocarboxylic acid or the like can be used. Of these, particularly preferable ones include acrylic acid, methacrylic acid, isobutyric acid, octylic acid, formic acid, glyoxylic acid, crotonic acid, acetic acid, propionic acid, benzoic acid, salicylic acid, cyclohexanecarboxylic acid, toluic acid, phenylacetic acid and p-t-butylbenzoic acid.

The reaction of the imidazole compound and the silane compound having a glycidoxy group is carried out using the synthesis method disclosed in Japanese Patent Application Laid-open No. H5-186479. Specifically, the imidazole compound and the silane compound having a glycidoxy group can be reacted by heating the imidazole compound to a temperature of 80 to 200° C. and then instilling the silane compound having a glycidoxy group into the imidazole compound in a ratio of 0.1 to 10 mol of the silane compound per 1 mol of the imidazole compound, and in this case the reaction time is adequate at about 5 minutes to 2 hours. There is no particular need for a solvent, but an organic solvent such as chloroform, dioxane, methanol or ethanol may be used as a reaction solvent. Note that the reaction is damaged by water, and is thus preferably proceeded under an atmosphere of a gas containing no moisture such as dried nitrogen or argon so that no moisture gets into the system. The desired imidazole-silane compound represented as the above general formula is obtained as a mixture with other compounds having siloxane bonds, but the desired compound can be isolated and purified by a known method that utilizes the difference in solubility between the compounds or column chromatography. Note, however, that in the case of use as a surface treatment agent or a resin additive, there is no real need to isolate the imidazole-silane compounds from one another, and the reaction mixture containing complex compounds partially networked through Si—O bonds can be used as it is in the next reaction step, namely the reaction with the organic monocarboxylic acid. The imidazole-silane compounds so obtained reacts with the organic monocarboxylic acid by heating the imidazole-silane compounds to a temperature of 50 to 200° C., and then adding, for example, an equivalent molar amount of the organic monocarboxylic acid; the reaction time is again adequate at about 5 minutes to 2 hours. Again, there is no particular need for a solvent, but an organic solvent such as chloroform, dioxane, methanol and ethanol may be used as a reaction solvent. Moreover, again the reaction is damaged by water, and is thus preferably advanced under an atmosphere of a gas containing no moisture such as dried nitrogen or argon so that no moisture gets into the system.

The imidazole/organic monocarboxylic acid salt derivative reaction product of the present invention usefully serves as a surface treatment agent or a resin additive for improving adhesion. When used as a surface treatment agent, the imidazole/organic monocarboxylic acid salt derivative reaction product of the present invention is preferably used as a solution with a suitable solvent. Moreover, when used as a resin additive, the reaction product may either be used as is or as a solution in a suitable solvent, with the amount added being 0.01 to 50 parts per weight, preferably 0.1 to 20 parts per weight, per 100 parts per weight of the resin. Moreover, substrates to which the surface treatment agent of the present invention can be applied include substrates made of a metallic material such as copper, iron or aluminum or an inorganic material such as glass fiber, silica, aluminum oxide or aluminum hydroxide. Moreover, when adding the imidazole/organic monocarboxylic acid salt derivative reaction product of the present invention to a resin to improve the adhesion and strength of the resin, resins that can be used include polyimide resins, phenol resins, urea resins, melamine resins, unsaturated polyester resins, diallyphthalate resins, polyurethane resins, silicon resins, vinyl chloride resins, vinylidene chloride resins, vinyl acetate resins, polyvinyl alcohol resins, polyvinyl acetal resins, polystyrene resins, AS resins, ABS resins, AXS resins, methacrylate resins, polyethylene resins, EVA resins, EVOH resins, polypropylene resins, fluororesins, polyamide resins, polyacetal resins, polycarbonate resins, saturated polyester resins, polyphenylene ether resins, polyphenylene sulfide resins, polyarylate resins, polysulfone resins, polyethersulfone resins, polyetheretherketone resins, liquid crystal plastic resins, cellulose plastic resins, thermoplastic elastomer resins, alkyd resins, furan resins, acrylic acid ester resins, petroleum resins, dicyclopentadiene resins, diethylene glycol bis(allyl carbonate) resins, and polyparabanic acid resins.

BEST MODE FOR CARRYING OUT THE INVENTION

Following is a more detailed description of the present invention with examples. Synthesis of the imidazole/organic carboxylic acid salt derivative

EXAMPLE 1

Figure 1:
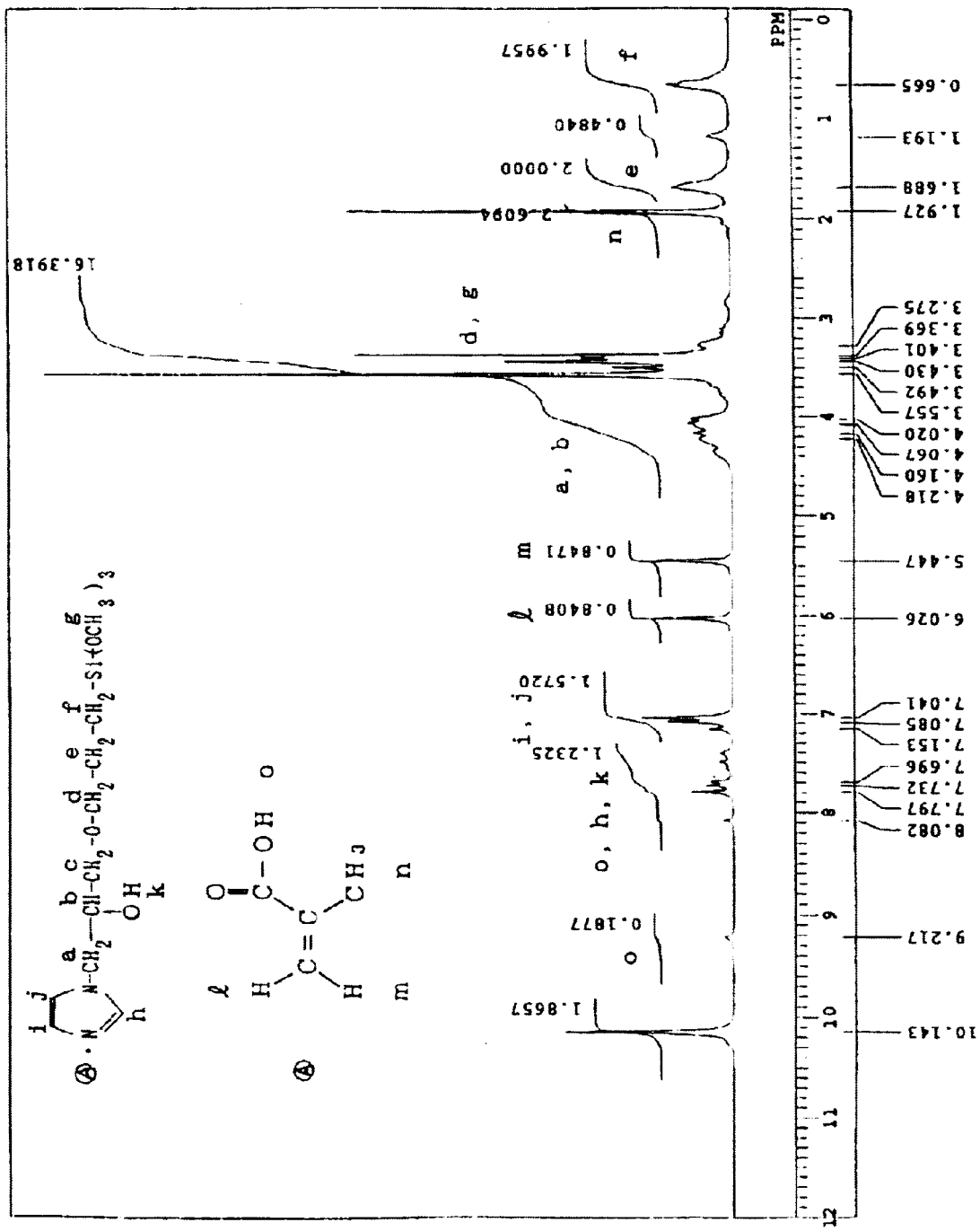
FIG. 1 is a $^1$H-NMR spectrum of the imidazole/methacrylic acid salt derivative synthesized in Example 1.
Figure 2:
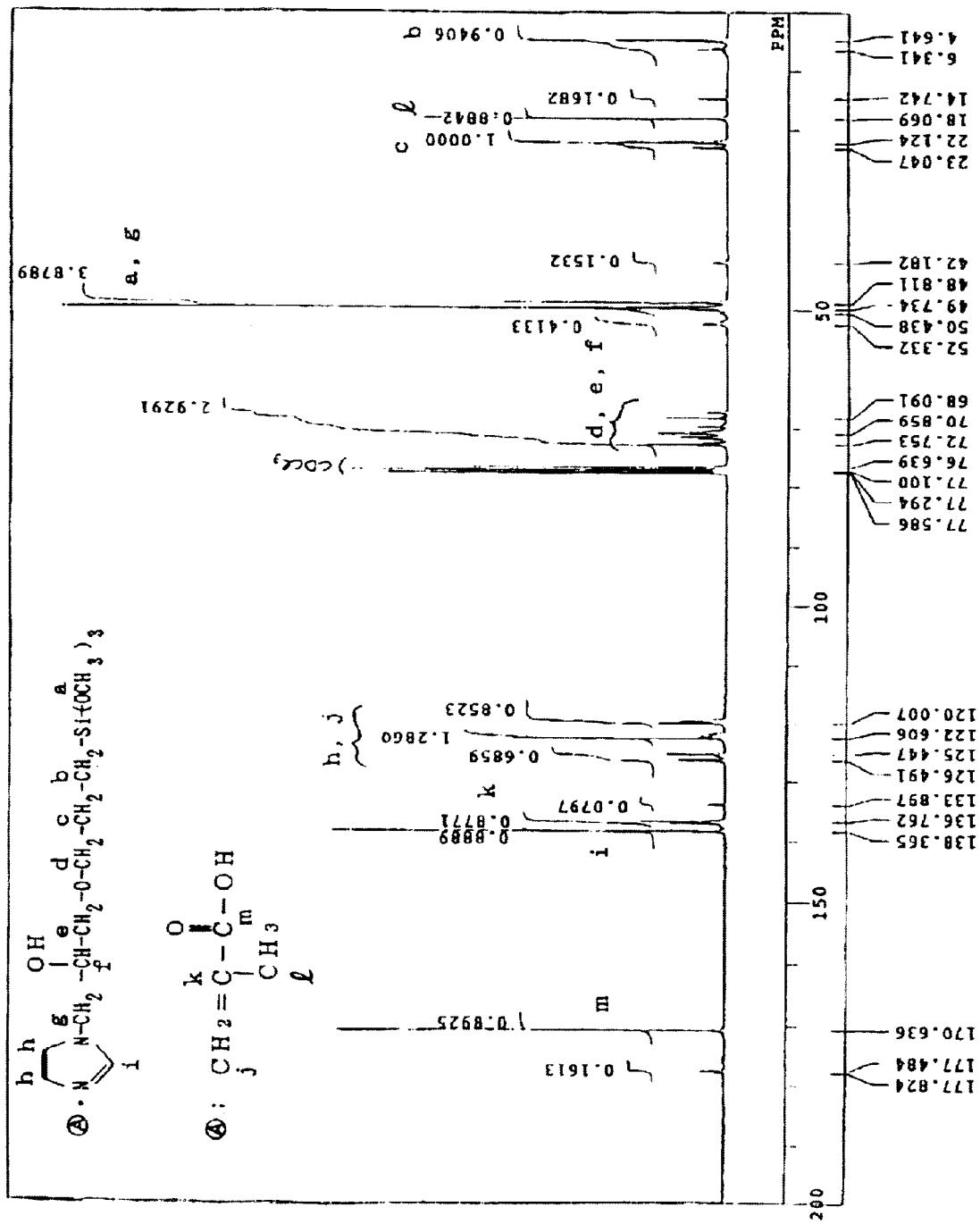
FIG. 2 is a $^{13}$C-NMR spectrum of the imidazole/methacrylic acid salt derivative synthesized in Example 1.
Figure 3:
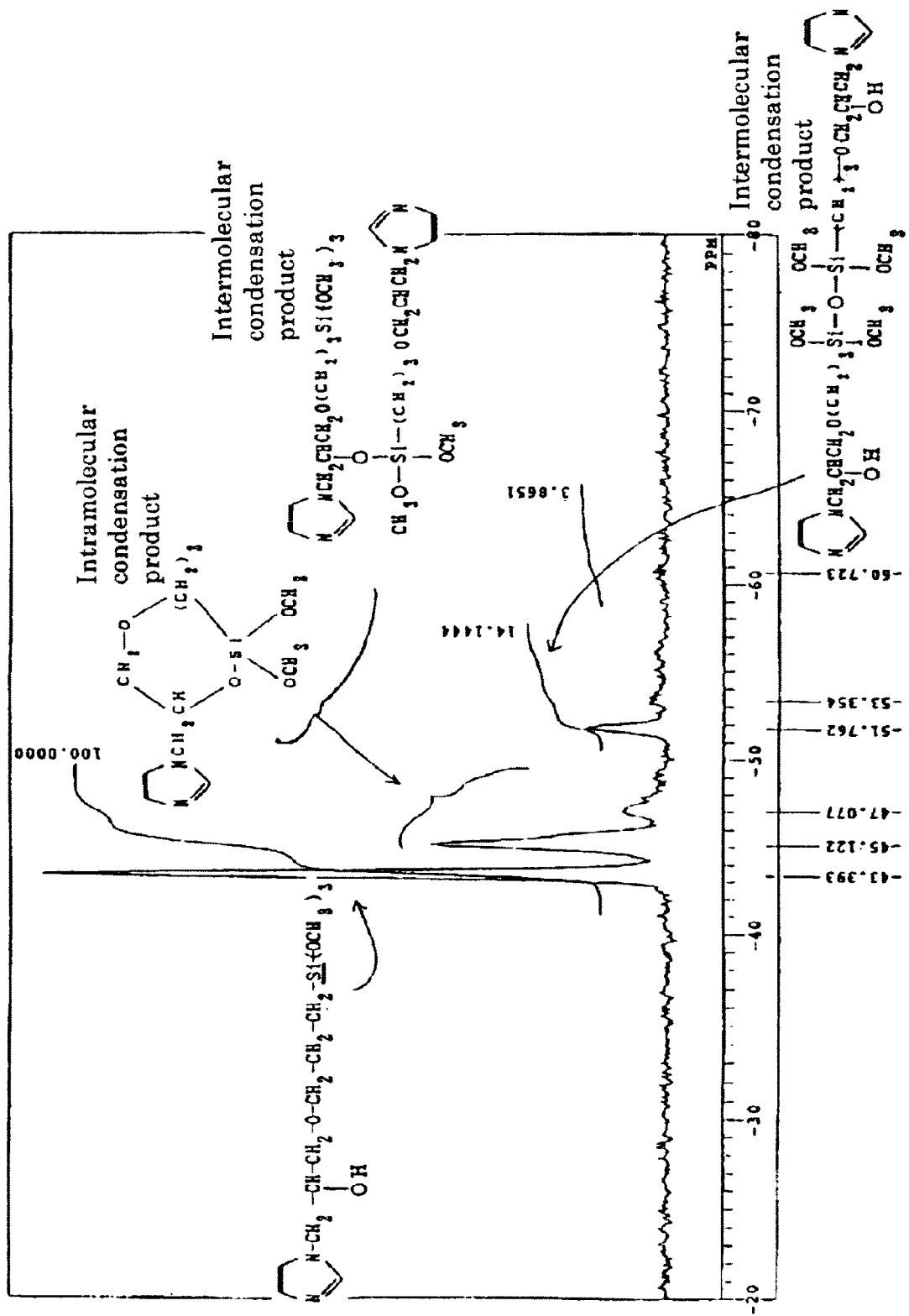
FIG. 3 is a $^{29}$Si-NMR spectrum of the imidazole/methacrylic acid salt derivative synthesized in Example 1.
Figure 4:
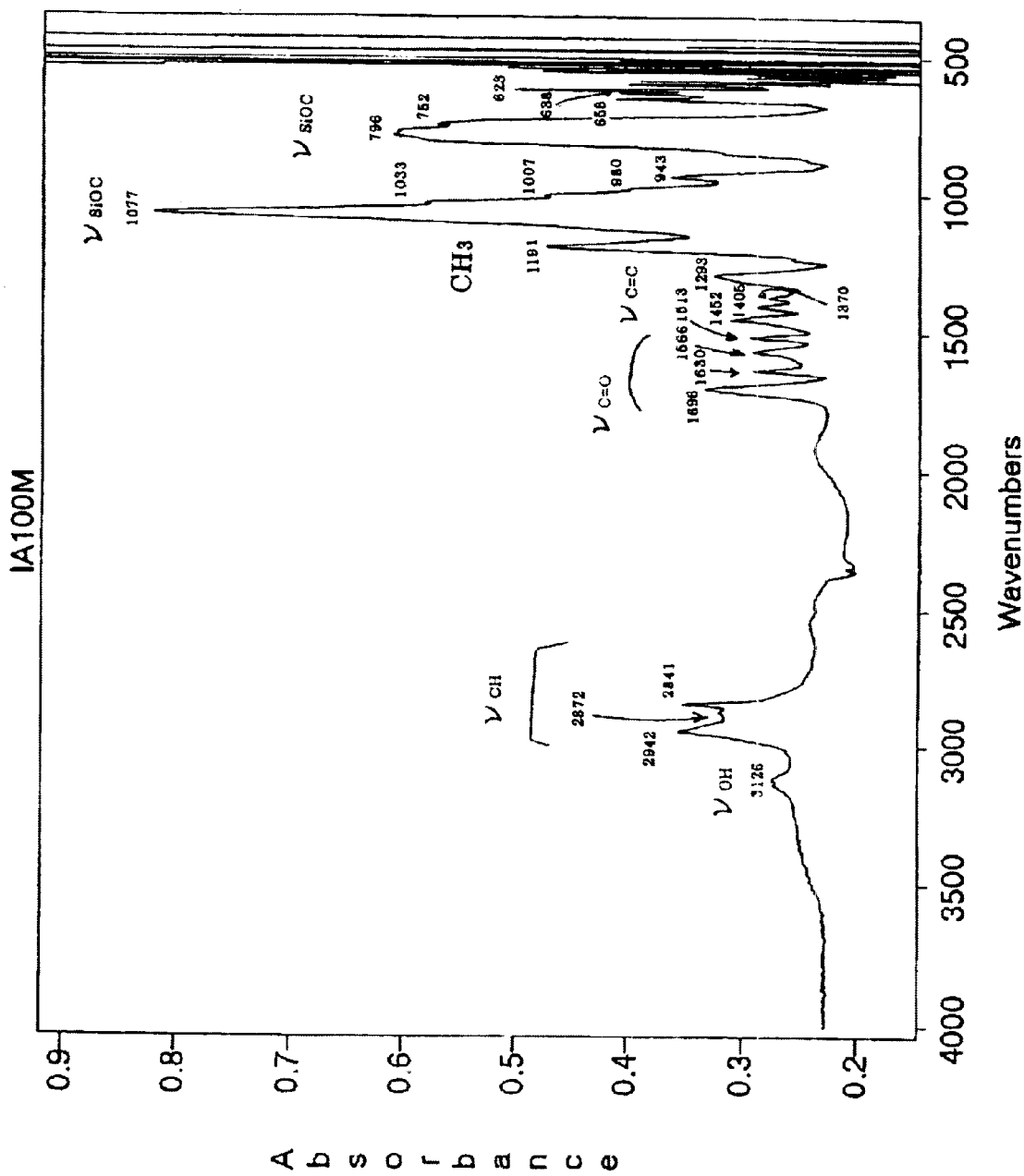
FIG. 4 is an FT-IR spectrum of the imidazole/methacrylic acid salt derivative synthesized in Example 1.

Imidazole 13.62 g (0.2 mol) was melted at 95° C., and 47.27 g (0.2 mol) of 3-glycidoxypropyltrimethoxysilane was instilled therein over 30 minutes while stirring under an argon atmosphere. After the instillation had been completed, the reaction was continued for a further 1 hour at a temperature of 95° C., thus obtaining imidazole-silane compounds. The reaction solution was then kept at a temperature of 80° C. while instilling therein 17.2 g (0.2 mol) of methacrylic acid over 30 minutes. After the instillation had been completed, the reaction was allowed to proceed for a further 30 minutes at a temperature of 80° C., thus obtaining a reaction product containing the compound represented by undermentioned formula (1—1) along with other complex compounds having siloxane bonds. The reaction product was obtained as a viscous transparent orange liquid. The $^1$H-NMR spectrum, $^{13}$C-NMR spectrum, $^{29}$Si-NMR spectrum and FT-IR spectrum of the obtained imidazole/methacrylic acid salt derivative are shown in FIGS. 1, 2, 3 and 4, respectively.

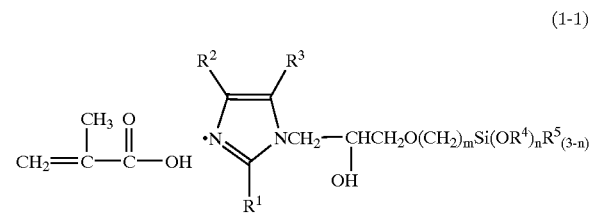

(1-1)

EXAMPLE 2

Imidazole 13.62 g (0.2 mol) was heated to 95° C., and 47.27 g (0.2 mol) of 3-glycidoxypropyltrimethoxysilane was instilled therein over 30 minutes while stirring under an argon atmosphere. After the instillation had been completed, the reaction was advanced for a further 1 hour at a temperature of 95° C., thus obtaining imidazole-silane compounds. The reaction solution was then kept at a temperature of 80° C. while adding therein 51.28 g (0.2 mol) of palmitic acid over 30 minutes. After the addition had been completed, the reaction was continued for a further 30 minutes at a temperature of 80° C., thus obtaining a reaction product containing the compound obtained in Example 1 but with palmitic acid substituted for methacrylic acid. The reaction product was obtained as a viscous transparent orange liquid.

EXAMPLE 3
Application as a Surface Treatment Agent (1)

Surfaces of aluminum alloy plates (A2024P made by Nihon Test Panels conforming to JIS H4000; size 25×100 mm, thickness 1.6 mm) were treated by immersing the plates in a 0.4% methanol solution of the imidazole/methacrylic acid salt derivative synthesized in above-mentioned Example 1 and then drying with a blow of hot air. Two such surface-treated aluminum alloy plates were bonded together using a resin composition (Epicote 828 (an epoxy resin made by Yuka Shell Epoxy) 100 parts; dicyandiamide (made by Kanto Kagaku) 5 parts; 2-ethyl-4-methylimidazole (made by Shikoku Kasei) 1 part) with curing conditions of 1 hour at 100° C. plus 1 hour at 150° C., and then a test for adhesive strength of the adhered samples against tensile shear was carried out in accordance with JIS K6850. Moreover, for comparison, untreated aluminum alloy plates and aluminum alloy plates treated with a 0.4% solution of 3-glycidoxypropyltrimethoxysilane in methanol were evaluated in the same way. The results are shown in Table 1.

TABLE 1

Test results of adhesive strength against tensile shear

| Treatment agent | Adhesive strength (KN/cm$^2$) |
|---|---|
| Imidazole/methacrylic acid salt derivative | 1.25 |
| 3-glycidoxypropyl-trimethoxysilane | 0.79 |
| Untreated | 0.75 |

Application as a Surface Treatment Agent (2) (Evaluation of Solubility)

The solubilities of the imidazole/organic monocarboxylic acid salt derivatives in various solvents were evaluated. The evaluation method was to bring the imidazole/organic monocarboxylic acid salt derivative into a solvent so as to be 1 wt %, and stir, and then visually observe whether or not the imidazole/organic monocarboxylic acid salt derivative dissolves. The results are shown in Table 2.

TABLE 2

Evaluation of solubility

| | Water | Methanol | Acetone | Ethyl acetate | Toluene | Hexane |
|---|---|---|---|---|---|---|
| Imidazole/ methacrylic acid salt derivative 1) | ○ | ○ | X | X | ○ | Δ |
| Imidazole/ palmitic acid salt derivative 2) | X | ○ | ○ | ○ | ○ | ○ |
| Imidazole-silane 3) | Δ4) | ○ | X | X | X | X |

1) The compound obtained in Example 1
2) The compound obtained in Example 2
3) Reaction product of imidazole and 3-glycidoxypropyltrimethoxysilane in Example 1
4) Goes cloudy if not added to water gradually in small amounts It is obvious from Table 2 that the imidazole/organic monocarboxyl acid salt derivatives obtained in Examples 1 and 2 exhibit superior solubility in various solvents compared with an imidazole-silane not modified with an organic monocarboxylic acid.

EXAMPLE 4
Application as a Resin Additive (1) (Improvement in Adhesion)

Two untreated aluminum alloy plates were bonded together using an epoxy resin composition (Epicote 828 100 parts; dicyandiamide (made by Kanto Kagaku) 5 parts; the imidazole/methacrylic acid salt derivative obtained in Example 1, 1 part) with curing conditions of 1 hour at 100° C. plus 1 hour at 150° C., and then an adhesive strength of the adhered plates against tensile shear was tested in accordance with JIS K6850. The results are shown in Table 3. Moreover, for comparison, another sample adhered using 1 part of 2-ethyl-4-methylimidazole in place of the imidazole/carboxylic acid salt derivative was evaluated in the same way. The results are shown in Table 3.

TABLE 3

Test results of adhesive strength against tensile shear

| Additive | Adhesive strength (KN/cm$^2$) |
|---|---|
| Imidazole/methacrylic acid salt derivative | 1.18 |
| 2-ethyl-4-methyl-imidazole | 0.75 |

Application as a Resin Additive (2) (Improvement in Mechanical Strength)

Epicote 828 (a bisphenol A type epoxy resin) made by Yuka Shell Epoxy was used as a resin, 11.28 g (2.89×10$^{-2}$ mol) of the imidazole/methacrylic acid salt derivative obtained in Example 1 was mixed in as a curing agent per 100 g of the epoxy resin, the mixture was cured with conditions of 1 hour at 100° C. plus 1 hour at 150° C. to produce a cured epoxy resin, and then the flexural strength was measured. The results are shown in Table 4. Moreover, for comparison, the same evaluation was carried out using an epoxy resin cured with 2-ethyl-4-methylimidazole, which is a commonly used imidazole curing agent.

TABLE 4

Improvement in mechanical strength

| Curing agent | Flexural strength (N/mm²) |
| --- | --- |
| Imidazole/methacrylic acid salt derivative | 105.2 |
| 2-ethyl-4-methyl-imidazole | 99.9 |

Application as a Resin Additive (3) (Improvement in Adhesive Strength)

The imidazole/methacrylic acid salt derivative obtained in Example 1 was added to a 20 wt % solution of a polyimide precursor having a polyamidic acid (a polymer obtained by reacting diamino diphenyl ether with pyromellitic acid anhydride) as the main constituent thereof in N-methylpyrrolidone such that the amount of the imidazole/methacrylic acid salt derivative relative to the resin was 1 wt %, and the resulting mixture was cast onto the lustrous surface of a piece of 1 oz copper foil. The cast film was cured under heating conditions of 30 minutes at 120° C., followed by 10 minutes at 150° C., followed by 10 minutes at 200° C., followed by 10 minutes at 250° C., followed by 10 minutes at 350° C., thus forming a 25-micron polyimide coating film on the copper foil. The adhesive strength of the laminate so obtained was then evaluated as the peel strength. The results were as follows.

| | Peel strength (kg/cm) |
| --- | --- |
| Imidazole/methacrylic acid salt derivative added | 1.2 |
| Imidazole/methacrylic acid salt derivative not added | 0.5 |

INDUSTRIAL APPLICABILITY

By using the imidazole/organic monocarboxylic acid salt derivative of the present invention as a surface treatment agent or a resin additive, the adhesion between a metal and a resin is improved. The imidazole/organic monocarboxylic acid salt derivative of the present invention is thus ideal for use in adhesives, encapsulants, coating materials, laminate materials, molding materials, printed circuit boards, semiconductor chip coating materials, semiconductor chip mounting materials, photosensitive materials such as photoresists, and the like when adhesiveness is important. Moreover, the imidazole/organic monocarboxylic acid salt derivative of the present invention can be used as a curing agent for a resin, improving the adhesive strength and the mechanical strength of the resin.

What is claimed is:

1. An imidazole/organic monocarboxylic acid salt derivative reaction product comprising a compound of formula (3),

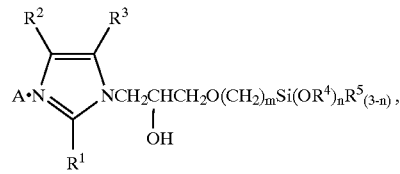

wherein A, is selected from the group consisting of a saturated monocarboxylic acid, an unsaturated aliphatic monocarboxylic acid and monocarboxylic acid, obtained reacting an imidazole compound represented by general formula (1) with a silane compound having a glycidoxy group represented by general formula (2) at 80 to 200° C. to form a first reaction product and then reacting the first reaction product with a member selected from the group consisting of a saturated aliphatic monocarboxylic acid, an unsaturated aliphatic monocarboxylic acid and an aromatic monocarboxylic acid at 50 to 200° C. to form the imidazole/organic monocarboxylic acid salt derivative reaction product,

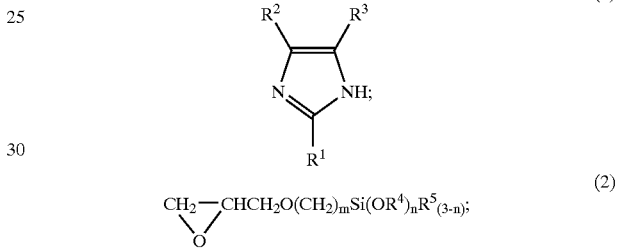

wherein $R^1$, $R^2$ and $R^3$ are each independently a hydrogen atom, a vinyl group or an alkyl group having 1 to 20 carbon atoms, $R^2$ and $R^3$ may together form an aromatic ring, $R^4$, and $R^5$ are each independently an alkyl group having 1 to 5 carbon atoms, m is an integer between 1 and 10 and n is an integer between 1 and 3.

2. The imidazole/organic monocarboxylic acid salt derivative reaction product of claim 1, wherein the organic monocarboxylic acid is selected from the group consisting of acrylic acid, methacrylic acid, isobutyric acid, octylic acid, formic acid, glyoxylic acid, crotonic acid, acetic acid, propionic acid, benzoic acid, salicyclic acid, cyclohexanecarboxylic acid, toluic acid, phenylacetic acid and p-t-butylbenzoic acid.

3. The imidazole/organic monocarboxylic acid salt derivative reaction product of claim 1, comprising:

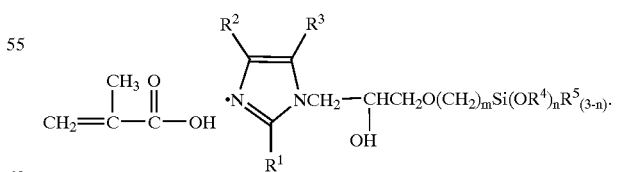

* * * * *